US008578284B2

(12) United States Patent
Takemura et al.

(10) Patent No.: US 8,578,284 B2
(45) Date of Patent: Nov. 5, 2013

(54) HARDNESS TESTING DEVICE WITH A USER INTERFACE FOR SETTING TEST LOCATIONS

(75) Inventors: Fumihiro Takemura, Kawasaki (JP); Kozo Ariga, Tokyo (JP)

(73) Assignee: Mitutoyo Corporation, Kanagawa (JP)

( * ) Notice: Subject to any disclaimer, the term of this patent is extended or adjusted under 35 U.S.C. 154(b) by 272 days.

(21) Appl. No.: 13/238,022

(22) Filed: Sep. 21, 2011

(65) Prior Publication Data

US 2012/0085154 A1    Apr. 12, 2012

(30) Foreign Application Priority Data

Oct. 6, 2010    (JP) .................................. 2010-226296

(51) Int. Cl.
*G01N 3/48*     (2006.01)
*G06F 3/048*    (2013.01)
*G01N 3/42*     (2006.01)
*G06F 9/44*     (2006.01)

(52) U.S. Cl.
CPC ................ *G01N 3/42* (2013.01); *G06F 9/4443* (2013.01)
USPC ........ 715/765; 73/78; 73/81; 73/82; 715/764; 715/810

(58) Field of Classification Search
USPC .......................... 73/78–85; 715/764, 765, 810
See application file for complete search history.

(56) References Cited

U.S. PATENT DOCUMENTS

| 4,627,096 | A | * | 12/1986 | Grattoni et al. ............... 382/141 |
| 5,146,779 | A | * | 9/1992 | Sugimoto et al. .................. 73/81 |
| 5,284,049 | A | * | 2/1994 | Fukumoto ........................ 73/82 |
| 7,121,136 | B2 | * | 10/2006 | Tsujii et al. ........................ 73/81 |
| 7,380,443 | B2 | * | 6/2008 | Tsujii et al. ........................ 73/81 |
| 2004/0096093 | A1 | * | 5/2004 | Hauck et al. ................... 382/141 |
| 2004/0134263 | A1 | * | 7/2004 | Tsujii et al. ........................ 73/81 |
| 2005/0081608 | A1 | * | 4/2005 | Shoelson ........................ 73/105 |
| 2006/0288763 | A1 | * | 12/2006 | Tsujii et al. ........................ 73/81 |
| 2013/0125631 | A1 | * | 5/2013 | Sadahiro .......................... 73/81 |

FOREIGN PATENT DOCUMENTS

| FR | 2619917 A1 * | 3/1989 | ............... G01N 3/42 |
| JP | 63298024 A * | 12/1988 | ............... G01N 3/42 |
| JP | 2003-166923 | 6/2003 | |

OTHER PUBLICATIONS

U.S. Appl. No. 13/238,014 to Fumihiro Takemura et al., filed Sep. 21, 2011.
U.S. Appl. No. 13/226,687 to Takeshi Sawa et al., filed Sep. 7, 2011.

* cited by examiner

*Primary Examiner* — David A Rogers
(74) *Attorney, Agent, or Firm* — Greenblum & Bernstein, P.L.C.

(57) ABSTRACT

A hardness tester includes a monitor capable of displaying a main screen and an assistant screen; a first test location setter setting an indentation formation location on a test specimen for an initial test; and a second test location setter setting an indentation formation location on the test specimen for a retest. The second test location setter judges whether a new indentation formation location is suitable for a test based on a surface image of the test specimen and a setting condition obtained during the initial test, and, in a case where it is judged that the new indentation formation location is unsuitable for a test, sets again a coordinate point different from the coordinate point of the new indentation formation location as another new indentation formation location.

6 Claims, 12 Drawing Sheets

HARDNESS TESTING DEVICE WITH A USER INTERFACE FOR SETTING TEST LOCATIONS

CROSS-REFERENCE TO RELATED APPLICATIONS

The present application claims priority under 35 U.S.C. §119 of Japanese Application No. 2010-226296, filed on Oct. 6, 2010, the disclosure of which is expressly incorporated by reference herein in its entirety.

BACKGROUND OF THE INVENTION

1. Field of the Invention

The present invention relates to a hardness tester.

2. Description of Related Art

Conventionally, a hardness tester is known, in which an indenter loaded with a predetermined load is pressed against a surface of a test specimen to form an indentation, and hardness of the test specimen is evaluated based on a diagonal length of the indentation and the loaded load (for example, see Japanese Patent Laid-Open Publication No. 2003-166923). In such a hardness tester, for example, in a case where a same test is performed with respect to a plurality of test specimens, a test method is known in which, first, during a test with respect to a first test specimen, a coordinate system is set at a predetermined location on the test specimen, and a test procedure for performing a test at a predetermined point in the coordinate system is stored; and, with respect to a subsequent test specimen, when a coordinate system is set, the stored test procedure is used to repeat the same test as that performed with respect to the first test specimen.

However, in a case where a clearly incorrect measured value or the like is obtained due to some reason in a hardness test, a retest may be performed with respect to a test specimen that has been tested once. It is desirable that the retest be performed under the same condition as that for the first test. Therefore, there is a demand for performing a test using a test method as described above.

However, in a hardness test, an indentation is formed on a test specimen during a test. Therefore, when a retest is performed, the test cannot be performed at the same location on the test specimen. Therefore, when performing a retest with respect to a test specimen that has been tested once, the stored test procedure cannot be used as-is. For example, an operation is necessary to manually avoid a location where an indentation has been previously formed. Thus, there is a problem that operability is poor.

SUMMARY OF THE INVENTION

A feature of the present invention is to improve the operability of a hardness tester for the case where a retest is performed with respect to a test specimen that has been tested once.

One aspect of the present invention is a hardness tester for forming an indentation on a surface of a test specimen mounted on a test specimen stage by pressing an indenter loaded with a predetermined load against the surface of the test specimen. The hardness tester includes a display, a first test location setter, and a second test location setter. The display is capable of displaying a main screen and an assistant screen, the main screen displaying a surface image of the test specimen, which is to have an indentation formed thereon by using the indenter, and the assistant screen displaying an assistant image to assist a user. The first test location setter sets a test location on the test specimen in a case where an initial test is performed with respect to the test specimen. The second test location setter sets a test location on the test specimen in a case where a retest is performed with respect to the test specimen. The first test location setter includes a first coordinate setter, an indentation formation location setter, a setting condition storage, and an image storage. The first coordinate setter sets a reference coordinate on the surface image of the test specimen in a case where the surface image of the test specimen is displayed in the main screen. The indentation formation location setter sets a coordinate point of an indentation formation location after the reference coordinate is set by the first coordinate setter. The setting condition storage stores a setting condition of the coordinate point set by the indentation formation location setter. The image storage stores the surface image of the test specimen displayed in the main screen. The second test location setter includes an assistant image display controller, a new indentation formation location setter, and a judger. The assistant image display controller displays the surface image of the test specimen stored in the image storage in the assistant screen as an assistant image. The new indentation formation location setter sets a coordinate point with respect to the assistant image as a new indentation formation location based on the setting condition stored in the setting condition storage in a case where a retest start instruction operation is performed by a user, the coordinate point being different from the coordinate point set by the indentation formation location setter. The judger judges whether the coordinate point of the new indentation formation location set by the new indentation formation location setter is suitable for a hardness test based on a brightness value of the surface image of the test specimen stored in the image storage. In a case where the coordinate point of the set new indentation formation location is judged as unsuitable for a hardness test by the judger, the new indentation formation location setter again sets a coordinate point of a new indentation formation location.

In another aspect of the present invention, in the above hardness tester, the new indentation formation location setter includes a distance calculator and a new indentation formation location selector. The distance calculator calculates a distance from an edge of the test specimen to the coordinate point set by the indentation formation location setter based on the setting condition stored in the setting condition storage in the case where the retest start instruction operation is performed by the user. The new indentation formation location selector selects as a new indentation formation location on the test specimen a coordinate point that has a distance from the edge of the test specimen equal to the distance calculated by the distance calculator and is different from the coordinate point set by the indentation formation location setter.

In another aspect of the present invention, in the above hardness tester, in a case where coordinate points of two points having equal distances from the edge of the test specimen are set as indentation formation locations by the indentation formation location setter, the new indentation formation location selector selects as a new indentation formation location a coordinate point of a midpoint of the two points on a line connecting the two points along a shape of the edge of the test specimen.

In another aspect of the present invention, the above hardness tester includes a selector selecting an automatic mode, in which a new indentation formation location is set by the new indentation formation location setter, and a manual mode, in which a new indentation formation location is set by a user at will. The second test location setter further includes a new indentation formation location determiner determining a new indentation formation location in response to a retest location specifying operation by a user with respect to the surface image of the test specimen displayed in the main screen in a case where the manual mode is selected by the selector.

According to the present invention, in the case where a retest is performed, based on the setting condition stored in the setting condition storage, a coordinate point different from the coordinate point of the indentation formation location on the test specimen is set as a new indentation formation location on the test specimen. Based on a brightness value of the surface image of the test specimen stored in the image storage, it is judged whether the new indentation formation location is suitable for a test. In a case where the new indentation formation location is judged as unsuitable for a test, a coordinate point different from the new coordinate point of the indentation formation location is set as another new indentation formation location. Thus, a location that is suitable as a new indentation formation location is automatically set, and a retest is performed. Therefore, operability can be improved in the case where a retest is performed with respect to a test specimen that has been tested once.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

Figure 1:
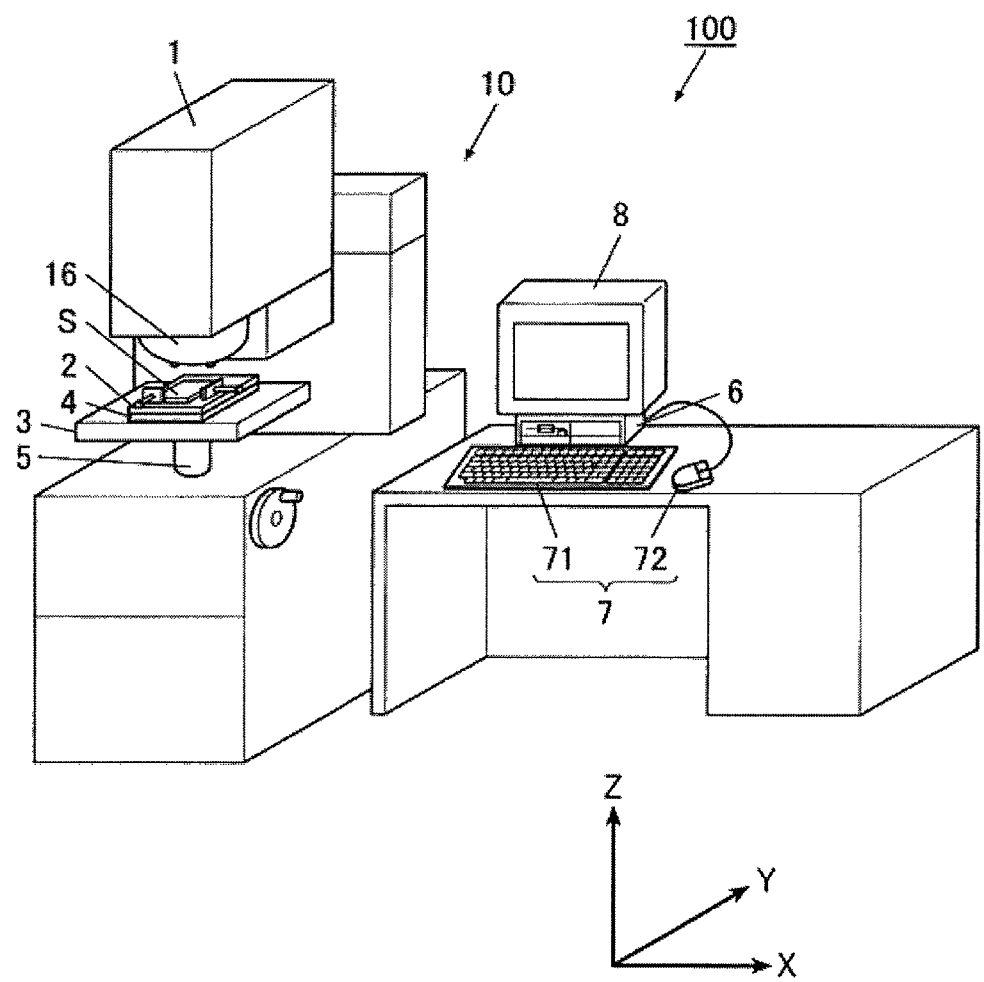
FIG. 1 is a schematic diagram illustrating an overall configuration of a hardness tester according to the present invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

In the following, with reference to the drawings, a hardness tester according to the present embodiment is explained in detail. In the following, a left-right direction, a front-back direction, and a height-wise direction of the hardness tester are respectively chosen as an X direction, a Y direction, and a Z direction.

A hardness tester 100 according to the present embodiment is a hardness tester capable of sequentially forming one or more indentations with respect to a test specimen S placed on a test specimen stage 2. The hardness tester 100 is capable of executing a "first test location setting process" setting an indentation formation location (test location) in a case where a first test (initial test) is performed with respect to the test specimen S, and a "second test location setting process" setting a new indentation formation location (retest location) in a case where a retest is performed with respect to the test specimen S. In the first test location setting process, a surface image of a test specimen S is captured and stored, and, at the same time, a setting condition of an indentation formation location that has been set with respect to the test specimen S is stored. In the second test location setting process, a new indentation formation location is set with respect to the test specimen S using the surface image of the test specimen S and the setting condition stored in the first test location setting process. This allows the hardness tester 100 to easily perform a retest with respect to the test specimen.

Specifically, the hardness tester 100 is, for example, a micro-Vickers hardness tester, and includes, as FIGS. 1-5 illustrate, a tester body 10, a controller 6, an operator 7, a monitor 8, and the like.

Figure 2:
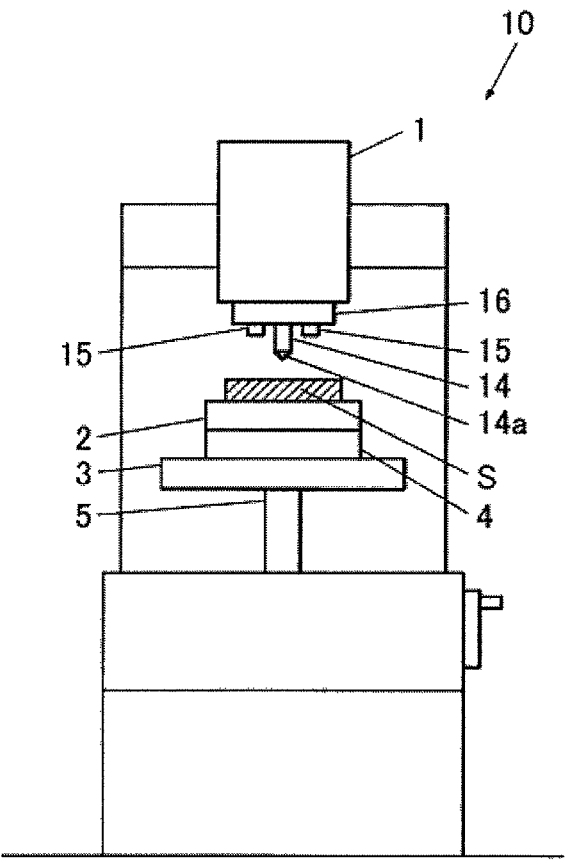
FIG. 2 is a schematic diagram illustrating a tester body of the hardness tester illustrated in FIG. 1.
Figure 2:
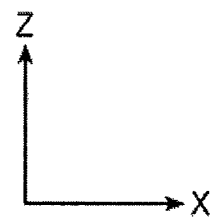
Figure 3:
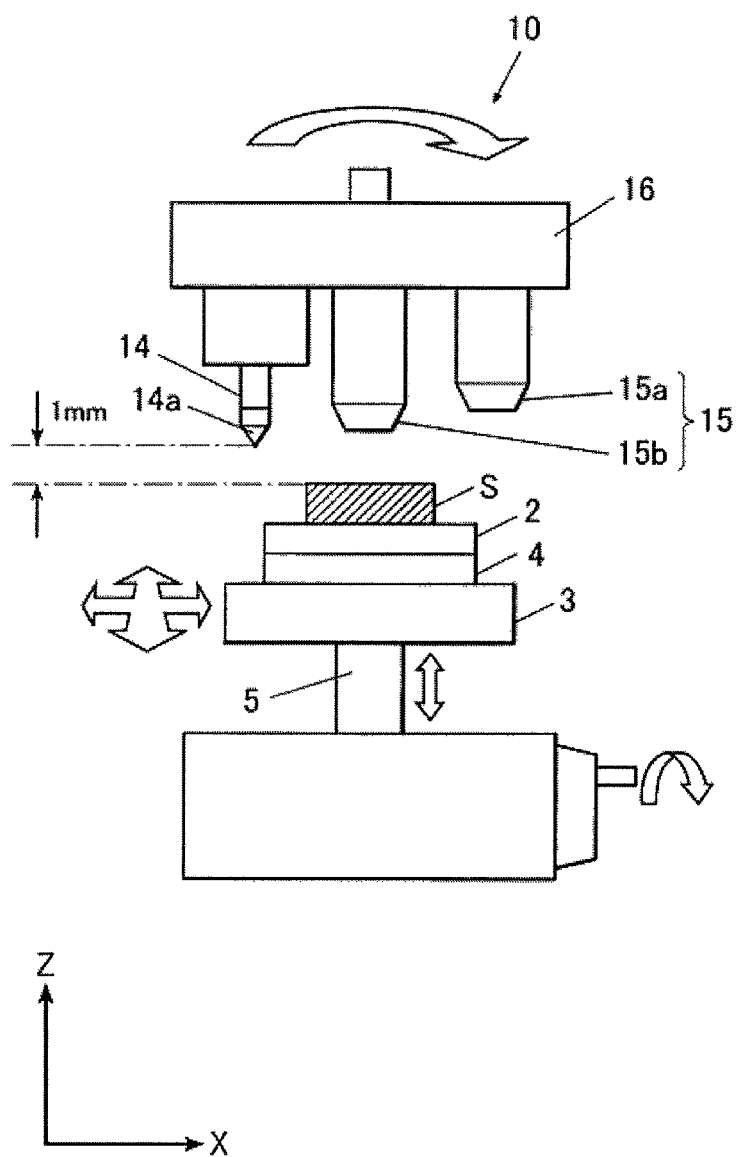
FIG. 3 is a schematic diagram illustrating a configuration of a key section of the hardness tester illustrated in FIG. 1.

The tester body 10, for example, as FIGS. 2 and 3 illustrate, includes a hardness measurer 1 performing hardness measurement of a test specimen S, a test specimen stage 2 holding the test specimen S, an XY stage 3 moving the test specimen stage 2, an AF (Z) stage 4 for focusing on a surface of the test specimen S, a lifting mechanism 5 moving the test specimen stage 2 (the XY stage 3, and the AF (Z) stage 4) up and down, and the like.

Figure 4:
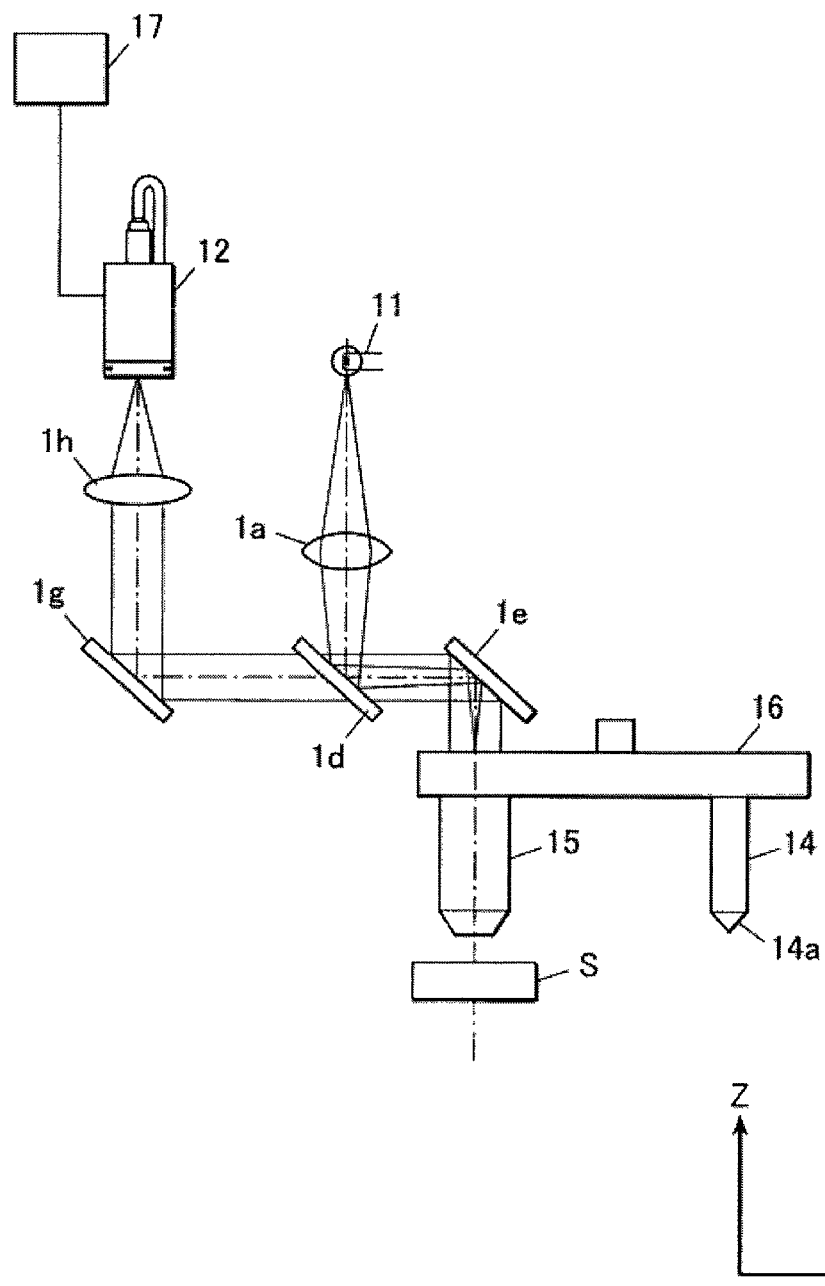
FIG. 4 is a schematic diagram illustrating a hardness measurer of the hardness tester illustrated in FIG. 1.

As FIG. 4 illustrates, for example, the hardness measurer 1 includes a lighting device 11 lighting the surface of the test specimen S, a CCD (Charge Coupled Device) camera 12 capturing an image of the surface of the test specimen S, an turret 16, and the like, the turret 16 including an indenter shaft 14, which has an indenter 14a, and an objective lens 15, and being capable of switching between the indenter shaft 14 and the objective lens 15 by rotation.

The lighting device 11 lights the surface of the test specimen S by radiating light. The light radiated from the lighting device 11 arrives at the surface of the test specimen S via a lens 1a, a half mirror 1d, a mirror 1e, and the objective lens 15.

The CCD camera 12 captures a surface image of the test specimen S mounted on the test specimen stage 2. Specifically, based on reflected light input from the surface of the test specimen S via the objective lens 15, the mirror 1e, the half mirror 1d, a mirror 1g, and a lens 1h, the CCD camera 12 captures images of the surface of the test specimen S and an indentation formed by using the indenter 14a on the surface of the test specimen S, obtains image data, and outputs the data to the controller 6 via a frame grabber 17, which is capable of simultaneously accumulating and storing image data of a plurality of frames.

The indenter shaft 14 is moved toward the test specimen S mounted on the test specimen stage 2 by a loading mechanism (not shown in the drawings), which is driven in response to a control signal output by the controller 6, and the indenter 14*a*, which is provided at an apical portion of the indenter shaft 14, is pressed against the surface of the test specimen S with a predetermined test force.

A plurality of objective lenses 15, which are respectively equipped with condenser lenses 15*a* and 15*b* of different magnifications, are held on a lower surface of the turret 16, and are positioned above a test specimen S by rotation of the turret 16, thereby causing light radiated from the lighting device 11 to uniformly irradiate the surface of the test specimen S.

The turret 16 is configured to have the indenter shaft 14 and the plurality of the objective lenses 15 attached on its lower surface, and be capable of switching any one of the indenter shaft 14 and the plurality of the objective lenses 15 to a position above the test specimen S by rotating around an axis in the Z axis direction. In other words, by lowering the indenter shaft 14 in a state in which the indenter shaft 14 is positioned above the test specimen S, an indentation is formed on the surface of the test specimen S; and, by positioning an objective lens 15 above the test specimen S, the formed indentation can be observed.

The test specimen stage 2 has the test specimen S mounted on its upper surface. The XY stage 3 is driven by a driving mechanism (not shown in the drawings), which is driven in response to a control signal output by the controller 6, and moves the test specimen stage 2 in a direction (the X axis direction and the Y axis direction) perpendicular to the movement direction (the Z axis direction) of the indenter 14*a*. The AF (Z) stage 4 is driven in response to a control signal output by the controller 6, and, based on the image data captured by the CCD camera 12, finely moves the test specimen stage 2 up and down to focus on the surface of the test specimen S. The lifting mechanism 5 is driven in response to a control signal output by the controller 6, and changes a relative distance between the test specimen stage 2 and the objective lens 15 by moving the test specimen stage 2 (the XY stage 3 and the AF (Z) stage 4) in the up-down direction.

The operator 7 includes a keyboard 71, a mouse 72, and the like, and allows a user to execute an input operation when performing a hardness test. When a predetermined input operation is performed by the operator 7, a predetermined operation signal corresponding to the input operation is output to the controller 6.

Specifically, for example, the operator 7 is operated as a selector when selecting whether to perform a retest in an automatic mode or a manual mode. Here, the automatic mode is a mode, in which a new indentation formation location is automatically set during a retest by a new indentation formation location setter (to be described later). The manual mode is a mode in which a new indentation formation location is specified by a user at will during a retest.

The operator 7 is operated when a user performs a "coordinate setting operation", an "indentation formation location setting operation", an "image read-out operation", a "retest start instruction operation", a "retest location specifying operation", and the like, with respect to a surface image of a test specimen S displayed in a main screen A1 (to be described later) on the monitor 8.

Here, the coordinate setting operation is an operation in which a user specifies a location that sets a reference coordinate for determining an indentation formation location with respect to the surface image of the test specimen S displayed in the main screen A1 on the monitor 8 in the first test location setting process. The indentation formation location setting operation is an operation in which a user specifies an indentation formation location with respect to the surface image of the test specimen S after the reference coordinate is set on the surface image of the test specimen S displayed in the main screen A1 on the monitor 8 in the first test location setting process.

The image read-out operation is an operation in which a user gives an instruction to read-out the surface image of the test specimen S captured during the initial test, in a case where a retest is performed with respect to a test specimen S with respect to which a hardness test has been performed once by the first test location setting process. The retest start instruction operation is an operation in which a user gives an instruction to start a retest. The retest location specifying operation is an operation in which a user specifies at will a new indentation formation location on the test specimen S in the case where a retest is manually performed.

In addition, the operator 7 is also used when a user performs setting for various conditions when the hardness tester 100 is used to perform a hardness test. Here, the setting for various conditions means, for example, setting for test conditions (values of a material property of a test specimen S, a test force (N) loaded on the test specimen S by the indenter 14*a*, magnification of the objective lens 15, and the like), a test starting point, numbers of rows and columns, a pitch, and the like.

The monitor 8 includes a display device, for example, such as an LCD (Liquid Crystal Display) and the like, and displays a setting condition input using the operator 7 for a hardness test, a result of the hardness test, a surface image of a test specimen S captured by the CCD camera 12, an image of an indentation formed on the surface of the test specimen S, and the like. This allows the monitor 8 to act as a display.

Here, a display screen displayed on the monitor 8 is explained with reference to FIGS. 6 and 7.

Figure 6:
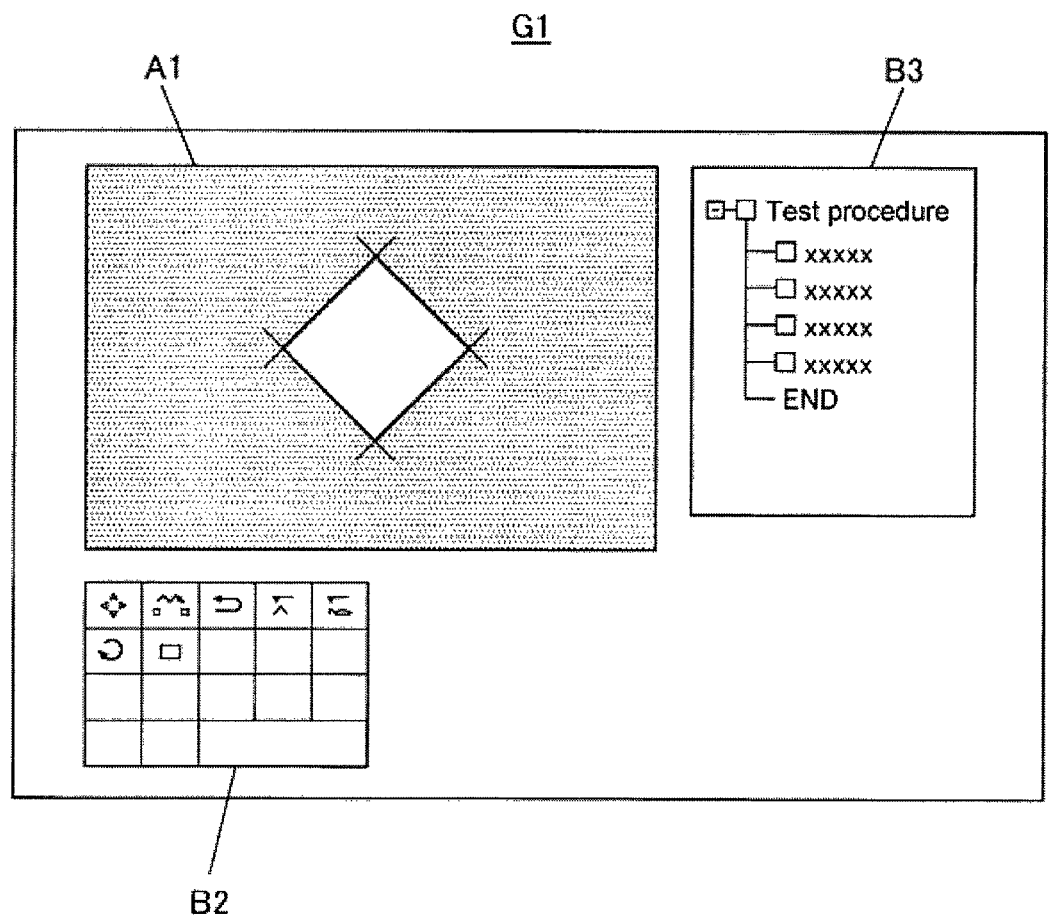
FIG. 6 illustrates an example of a display screen displayed on a monitor when an initial test is performed with respect to a test specimen.

FIG. 6 is an example of a display screen G1 displayed on the monitor 8 when an indentation is formed with respect to a test specimen S (when the first test location setting process is performed). The display screen G1 includes the main screen A1, a toolbox B2, a test procedure display area B3, and the like. In the display screen G1, the surface image of the test specimen S captured by the CCD camera 12 is displayed in the main screen A1. A high magnification lens is mounted in the CCD camera 12. Therefore, an enlarged image capturing a portion of a test specimen S is displayed in the main screen A1. In the toolbox B2, various tools for performing various operations such as the coordinate setting operation, the indentation formation location setting operation, and the like, are listed. When performing a coordinate setting operation, a user can select an appropriate tool and can specify any point in the main screen A1 by clicking on the main screen A1. When performing an indentation formation location setting operation, a user can select an appropriate tool and can specify any point in the main screen A1 as an indentation formation location by clicking on the main screen A1. In the test procedure display area B3, a test procedure to be performed with respect to the test specimen S during an initial test is displayed.

Figure 7:
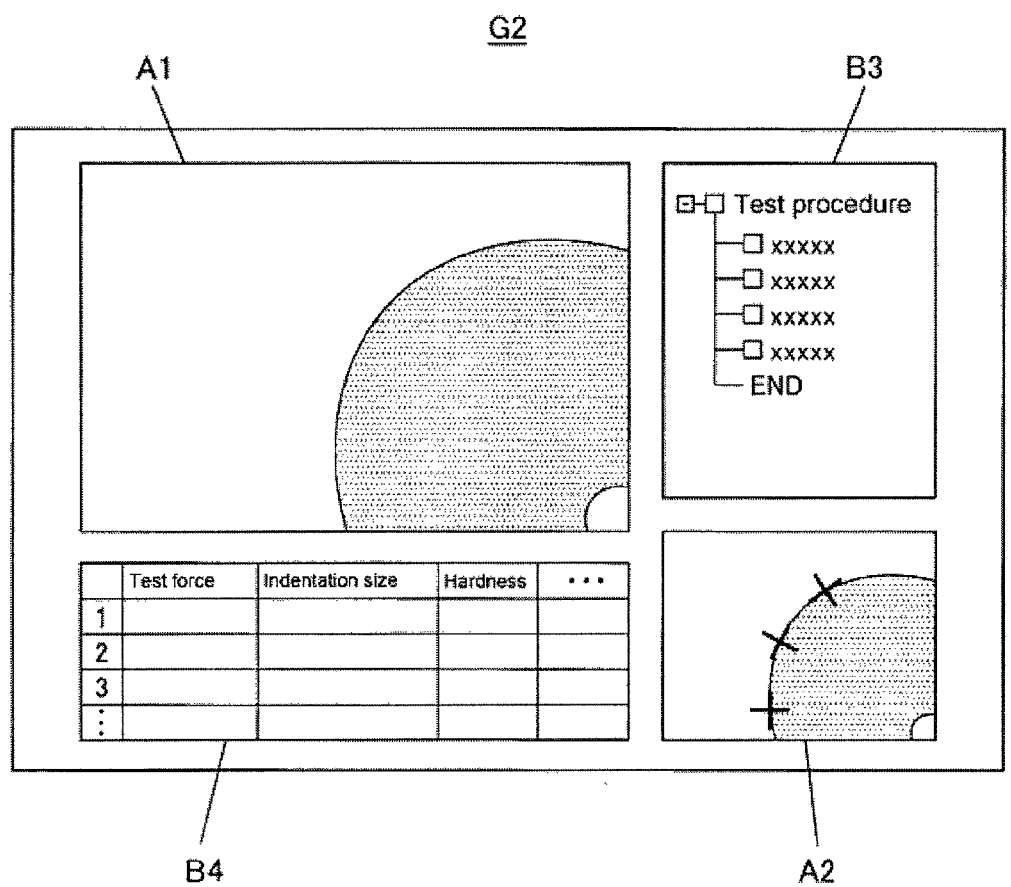
FIG. 7 illustrates an example of a display screen displayed on a monitor when an retest is performed with respect to a test specimen.

FIG. 7 is an example of a display screen G2 displayed on the monitor 8 when a retest is performed with respect to the test specimen S (when the second test location setting process is performed). The display screen G2 includes the main screen A1, an assistant screen A2, the test procedure display area B3, a test result display area B4, and the like. In the display screen G2, a surface image of a test specimen S to be retested (a test specimen that already has an indentation formed thereon) is captured by the CCD camera 12 and is displayed in the main screen A1. In the assistant screen A2, the surface image of the test specimen S captured during the initial test is displayed as an assistant image. The assistant screen A2 is a screen that is displayed on the monitor 8 and is used when the second test location setting process is performed, and displays the surface image of the test specimen S captured during the initial test in a case where a user performs an image read-out operation. In the test procedure display area B3, a test procedure prepared based on the indentation formation of the test specimen S during the initial test is listed. In the test result display area B4, test results such as a test force, a size of an indentation, hardness, and the like are displayed.

Figure 5:
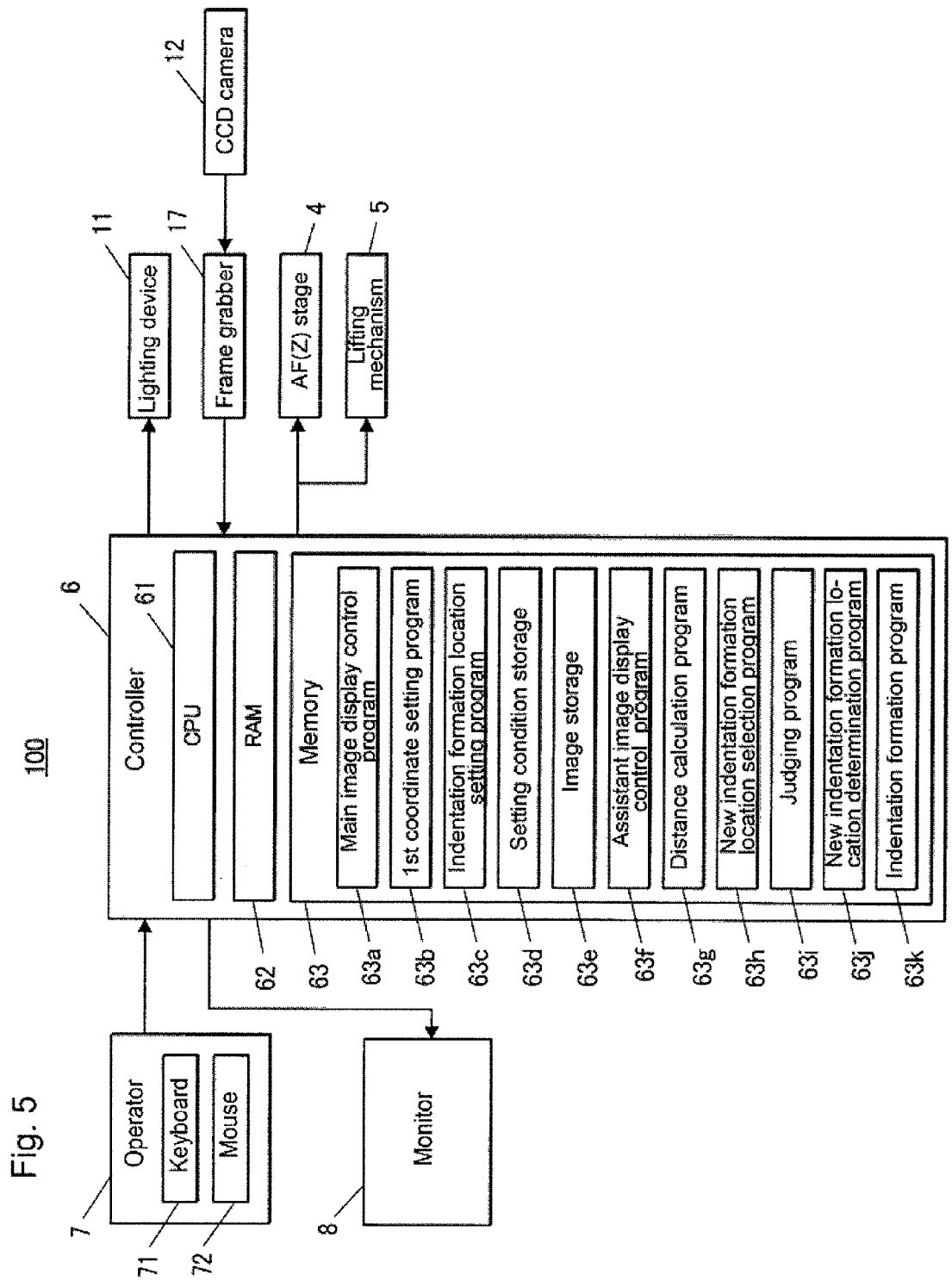
FIG. 5 is a block diagram illustrating a controlling mechanism of the hardness tester illustrated in FIG. 1.

The controller 6, as FIG. 5 illustrates, includes a CPU (Central Processing Unit) 61, a RAM (Random Access Memory) 62, a memory 63, and the like, and performs operation control and the like for performing a predetermined hardness test by executing a predetermined program stored in the memory 63.

The CPU 61 reads out a processing program and the like stored in the memory 63, deploys it in the RAM 62 and executes it, and thereby, controls the entire hardness tester 100.

The RAM 62 deploys, in a program storage area within the RAM 62, a processing program and the like to be executed by the CPU 61, and stores, in a data storage area, input data, a processing result generated when the processing program is executed, and the like.

The memory 63 includes a recording medium (not shown in the drawings) storing, for example, a program, data, and the like. The recording medium is composed of a semiconductor memory and the like. The memory 63 stores various data, various processing programs, data processed by executing the programs, and the like, for causing the CPU 61 to control the entire hardness tester 100.

More specifically, the memory 63 stores, for example, a main image display control program 63a, a first coordinate setting program 63b, an indentation formation location setting program 63c, a setting condition storage 63d, an image storage 63e, an assistant image display control program 63f, a distance calculation program 63g, a new indentation formation location selection program 63h, a judging program 63i, a new indentation formation location determination program 63j, an indentation formation program 63k, and the like.

The main image display control program 63a is a program that causes the CPU 61 to display a surface image of a test specimen S captured by the CCD camera 12 in the main screen A1. Here, the CPU 61 displays the display screen G1 on the monitor 8 in the case where an initial test with respect to a test specimen S is performed (the case where the first test location setting process is performed). When an image of a test specimen S is captured, the CPU 61 displays the surface image of the test specimen S in the main screen A1. At this time, the CPU 61 stores the surface image of the test specimen S as an initial image in the image storage 63e. Further, the CPU 61 displays the display screen G2 on the monitor 8 in the case where a retest with respect to the test specimen S is performed (the case where the second test location setting process is performed). When an image of a test specimen S to be retested is captured, the CPU 61 displays the surface image of the test specimen S to be retested in the main screen A1. By executing such a main image display control program 63a, the CPU 61 acts as a main image display controller.

The first coordinate setting program 63b is a program that causes the CPU 61 to set a reference coordinate on a surface image of a test specimen S in the case where the surface image of the test specimen S is displayed in the main screen A1. Here, as illustrated in FIGS. 8(a)-8(d), a case is described as an example where normal lines are set at an equal pitch with respect to an arc-shaped test specimen S, and indentations are formed at a plurality of locations (three locations here) on each of the normal lines.

Figure 8A:
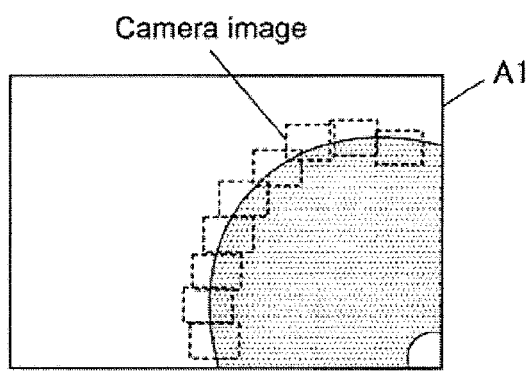
FIG. 8 illustrates an example of an image displayed in a main screen on a monitor when an initial test is performed.
Figure 8B:
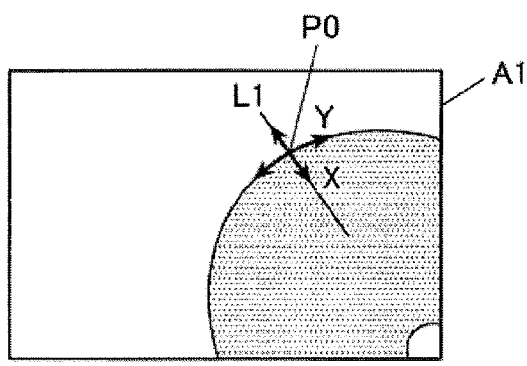
Figure 8C:
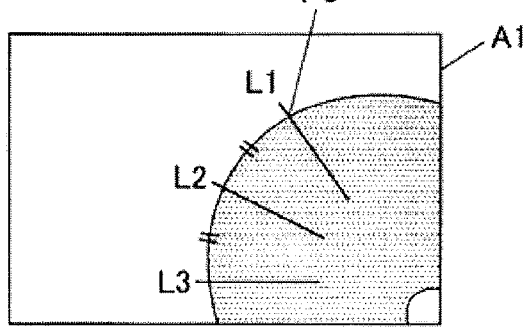

First, when an surface image of a test specimen S is displayed in the main screen A1, as illustrated in FIG. 8(a), the CPU 61 uses the CCD camera 12 and an autonomous contouring function to obtain a contour of an edge of the test specimen S. Next, as illustrated in FIG. 8(b), when, as a coordinate setting operation, a user clicks an arbitrary location on the edge of the test specimen S in the displayed image using a predetermined tool in the toolbox B2, the CPU 61 sets a reference line L1 along a normal direction from the clicked location. Here, the CPU 61 sets a reference coordinate by setting an X axis on the reference line L1 along the normal direction, and a Y axis along the shape of the edge of the test specimen S using the clicked location as a reference point P0 (0,0). Next, as illustrated in FIG. 8(c), the CPU 61 sets a predetermined number of reference lines along normal directions at a preset pitch along the edge of the test specimen S from the clicked location (the reference point P0). FIG. 8(c) is an example in which two reference lines L2 and L3 are set. At this time, the CPU 61 overlappingly displays the reference point P0, the reference lines L1-L3, and the reference coordinate on the surface image of the test specimen S using the main image display control program 63a, and stores this image in the image storage 63e.

In the present embodiment, a configuration is explained as an example in which the reference point P0, the reference lines L1-L3, and the reference coordinate are set in response to a coordinate setting operation performed by a user. However, a configuration is also possible in which the CPU 61 automatically sets these according to a preset condition after the contour of the edge of the test specimen S is obtained.

By executing such a first coordinate setting program 63b, the CPU 61 acts as a first coordinate setter.

Figure 8D:
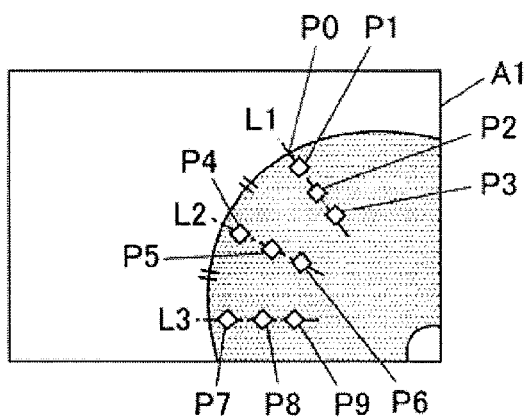

The indentation formation location setting program 63c is a program that causes the CPU 61 to set a coordinate point of an indentation formation location after a reference coordinate is set by executing the first coordinate setting program 63b. As illustrated in FIG. 8(d), when the reference coordinate is set with respect to the surface image of the test specimen S in the main screen A1, as an indentation formation location setting operation, a user clicks an arbitrary location on the reference line L1 using a predetermined tool in the toolbox B2. FIG. 8(d) is an example in which, as an indentation formation location setting operation, three points P1, P2, and P3 are specified by a user. When this is done, the CPU 61 calculates a coordinate point of a clicked location using the reference coordinate, and sets this coordinate point as an indentation formation location. Next, the CPU 61 calculates coordinate points of locations that have an equal distance from the edge of the test specimen S as that of the indentation formation location set on the reference line L1, and sets these coordinate points as coordinate points of indentation formation locations on the reference lines L2 and L3. FIG. 8(d) is an example in which, in accordance with the indentation formation location setting operation, the CPU 61 respectively sets P4-P6 and P7-P9 on the reference lines L2 and L3. When a coordinate point of an indentation formation location is set by executing such an indentation formation location setting program 63c, the CPU 61 executes the indentation formation program 63k (to be described later) to form an indentation on the test specimen S.

In the present embodiment, a configuration is explained as an example in which a coordinate point of an indentation formation location is set in response to an indentation formation location setting operation performed by a user. However, a configuration is also possible in which the CPU 61 automatically sets a coordinate point of an indentation formation location according to a preset condition after the X axis and the Y axis are set.

By executing such an indentation formation location setting program 63c, the CPU 61 acts as an indentation formation location setter.

The setting condition storage 63d, as a setting condition storage, stores a setting condition of a coordinate point set by the indentation formation location setting program 63c. The setting condition is a condition that indicates for what kind of shape an indentation is formed, and how such an indentation is formed. For example, here, a setting condition is stored so as to form three indentations (P1-3, P4-P6, and P7-9) on each of three normal lines (three reference lines L1-L3) lined up at an equal pitch, with respect to the edge of the arc-shaped test specimen S obtained using an automatic contouring function.

The image storage 63e, as an image storage, stores various images displayed in the main screen A1. Specifically, the image storage 63e stores the surface image (initial image) of the test specimen S. Further, the image storage 63e stores the image that overlappingly displays the location specified by the coordinate setting operation and the set reference coordinate on the initial image of the test specimen S. Further, the image storage 63e stores the surface image of the test specimen S having an indentation formed thereon by an initial test.

The assistant image display control program 63f is a program that causes the CPU 61 to display, in the assistant screen A2 as an assistant image, the surface image of the test specimen S stored in the image storage 63e. Specifically, in the case where a retest is performed (in a case where the second test location setting process is performed) with respect to the test specimen S, a user executes an image read-out operation. In response to such an operation, the CPU 61 displays, in the assistant screen A2 as an assistant image, the surface image of the test specimen S of the initial test stored in the image storage 63e. In this case, as an assistant image, it is desirable that the image overlappingly displaying the reference point P0, the reference lines L1-L3, the X and Y axes (reference coordinate), and the like on the initial image of the test specimen S be displayed. By executing such an assistant image display control program 63f, the CPU 61 acts as an assistant image display controller.

Figure 9A:
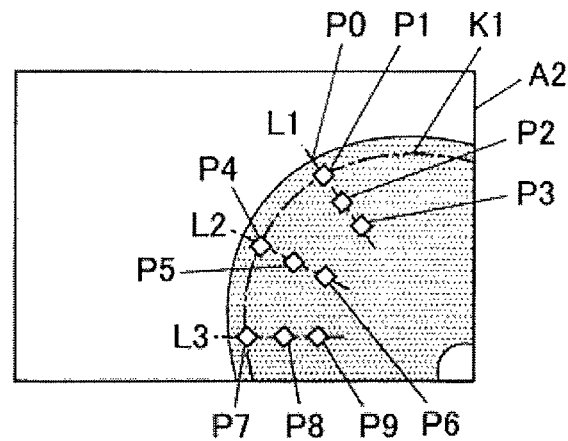
FIG. 9 illustrates an example of an image displayed in an assistant screen on a monitor when a retest is performed.

The distance calculation program 63g is a program that, in a case where a retest start instruction operation is performed by a user, causes the CPU 61 to calculate a distance of a coordinate point from the edge of the test specimen S based on the setting condition stored in the setting condition storage 63d, the coordinate point being set by executing the indentation formation location setting program 63c. Specifically, when a user performs a retest start instruction operation in a state in which an assistant image is displayed in the assistant screen A2, the CPU 61 calculates a distance (depth) from the edge of the test specimen S to each indentation based on the setting condition of the coordinate point stored in the setting condition storage 63d. In the present embodiment, as illustrated in FIG. 9(a), the depths of P1, P4, and P7 are the same. Further, the depths of P2, P5, and P8 are the same; and the depths of P3, P6, and P9 are the same. By executing such a distance calculation program 63g, the CPU 61 acts as a distance calculator.

Figure 9B:
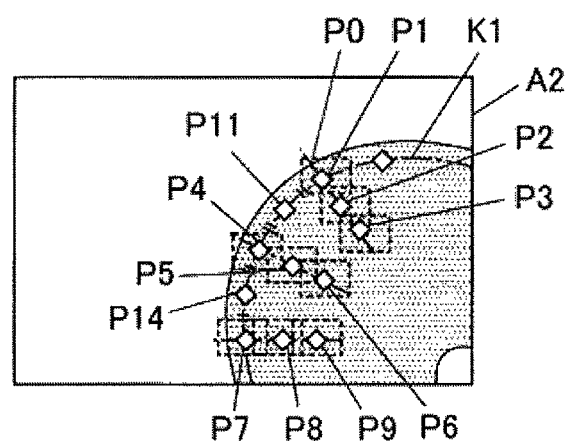
Figure 9C:
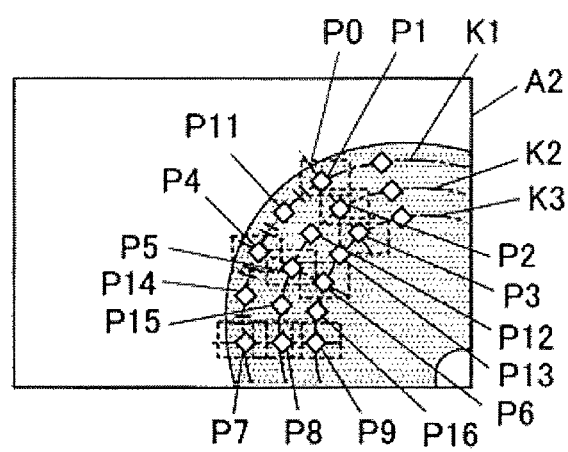

The new indentation formation location selection program 63h is a program that causes the CPU 61 to select a coordinate point as a new indentation formation location on the test specimen S that has a distance from the edge of the test specimen S equal to the distance calculated by executing the distance calculation program 63g and is different from the coordinate point set by executing the indentation formation location setting program 63c. Specifically, for example, as illustrated in FIG. 9(a), in a case where two or more coordinate points having equal distances from the edge of the test specimen S have been set as indentation formation locations, on a line connecting two adjacent two points along the shape of the edge of the test specimen S (imaginary lines K1-K3 in FIGS. 9(a)-9(c)), the CPU 61 selects a coordinate point of a point at the middle of the two points as a new indentation formation location. For example, as illustrated in FIG. 9(b), a midpoint P11 of the two points P1 and P4, a midpoint P14 of the two points P4 and P7, and the like are selected as new indentation formation locations. Further, as illustrated in FIG. 9(c), a midpoint P12 of the two points P2 and P5, a midpoint P13 of the two points P3 and P6, a midpoint P15 of the two points P5 and P8, a midpoint P16 of the two points P6 and P9, and the like are selected as new indentation formation locations. In this way, locations that are least affected by the indentations formed during the initial test are selected as new indentation formation locations.

Further, the new indentation formation location selection program 63h is a program that causes the CPU 61 to set again a coordinate point of a new indentation formation location in a case where a set coordinate point of a new indentation formation location is judged as unsuitable for a hardness test by executing the judging program 63i (to be described late). For example, in a case where a coordinate point of the midpoint P11 of the two points P1 and P4 is judged as unsuitable for a hardness test, the CPU 61 sets again a point on the imaginary line K1 excluding the midpoint P11 between the two points P1 and P4 as a new indentation formation location.

By executing such a new indentation formation location selection program 63h, the CPU 61 acts as a new indentation formation location selector.

The judging program 63i is a program that causes the CPU 61 to judge whether a coordinate point of a new indentation formation location set by executing the distance calculation program 63g and the new indentation formation location selection program 63h is suitable for a hardness test, based on a brightness value of the surface image of the test specimen S stored in the image storage 63e. Specifically, when a new indentation formation location is selected by executing the new indentation formation location selection program 63h, the CPU 61 calculates a brightness value of the new indentation formation location using the surface image of the test specimen S of the initial test stored in the image storage 63e. In a case where the calculated brightness value is less than a predetermined value, the CPU 61 judges that the new indentation formation location is unsuitable for a hardness test. In a case where it is judged that it is suitable for a hardness test by executing the judging program 63i, the CPU 61 executes the indentation formation program 63k (to be described later) to form an indentation at the new indentation formation location on the test specimen S. By executing such a judging program 63i, the CPU 61 acts as a judger.

The new indentation formation location determination program 63j is a program that causes the CPU 61 to determine a new indentation formation location with respect to a surface image of a test specimen S displayed in the main screen A1, in response to a retest location specifying operation by a user in the case where the manual mode is selected. Specifically, when performing a retest, in the case where the manual mode is selected by a user, the CPU 61 waits for a retest location specifying operation by the user with respect to the main screen A1, without executing the distance calculation program 63g. When the retest location specifying operation is performed, in response, the CPU 61 sets the specified location as a new indentation formation location. By executing such a new indentation formation location determination program 63*j*, the CPU 61 acts as a new indentation formation location determiner.

The indentation formation program 63*k* is a program that causes the CPU 61 to form an indentation on a test specimen S using the indenter 14*a*. Specifically, the CPU 61 forms an indentation with respect to a test specimen S during an initial test in the case where a coordinate point of an indentation formation location is set by executing the indentation formation location setting program 63*c*. At this time, the CPU 61 stores the surface image of the test specimen S having the indentation formed thereon in the image storage 63*e*. Further, in the case where it is judged by executing the judging program 63*i* that it is suitable for a hardness test, and in the case where an indentation formation location is determined in a manual mode by executing the new indentation formation location determination program 63*j*, the CPU 61 forms an indentation with respect to the test specimen S during a retest. By executing such an indentation formation program 63*k*, the CPU 61 acts as an indentation former.

The first coordinate setting program 63*b*, the indentation formation location setting program 63*c*, the setting condition storage 63*d*, the image storage 63*e*, and the like, constitute a first test location setter, which, in the case where an initial test is performed with respect to a test specimen S, sets an indentation formation location on the test specimen S. The distance calculation program 63*g*, the new indentation formation location selection program 63*h*, and the like, constitute a new indentation formation location setter. In the case where a retest start instruction operation is performed by a user, the new indentation formation location setter sets as a new indentation formation location a coordinate point that is different from the coordinate point set by executing the indentation formation location setting program 63*c*, with respect to the assistant image displayed in the assistant screen A2 and based on the setting condition stored in the setting condition storage 63*d*. The assistant image display control program 63*f*, the new indentation formation location setter, the judging program 63*i*, and the like, constitute a second test location setter, which, in the case where a retest is performed with respect to a test specimen S, sets an indentation formation location on the test specimen S.

Figure 10:
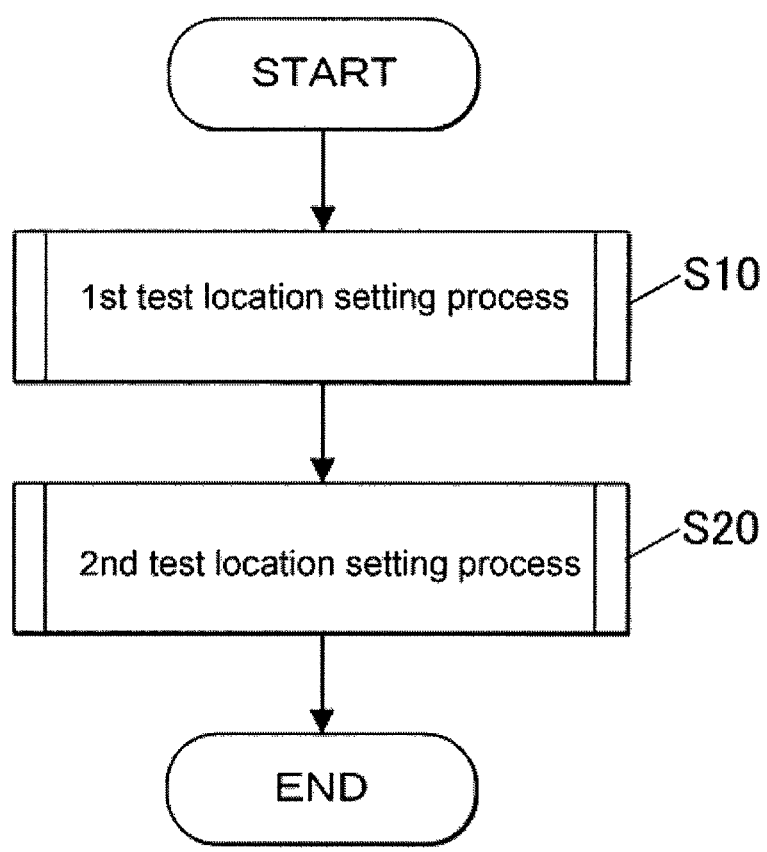
FIG. 10 is a flowchart for explaining a measurement process using the hardness tester illustrated in FIG. 1.
Figure 11:
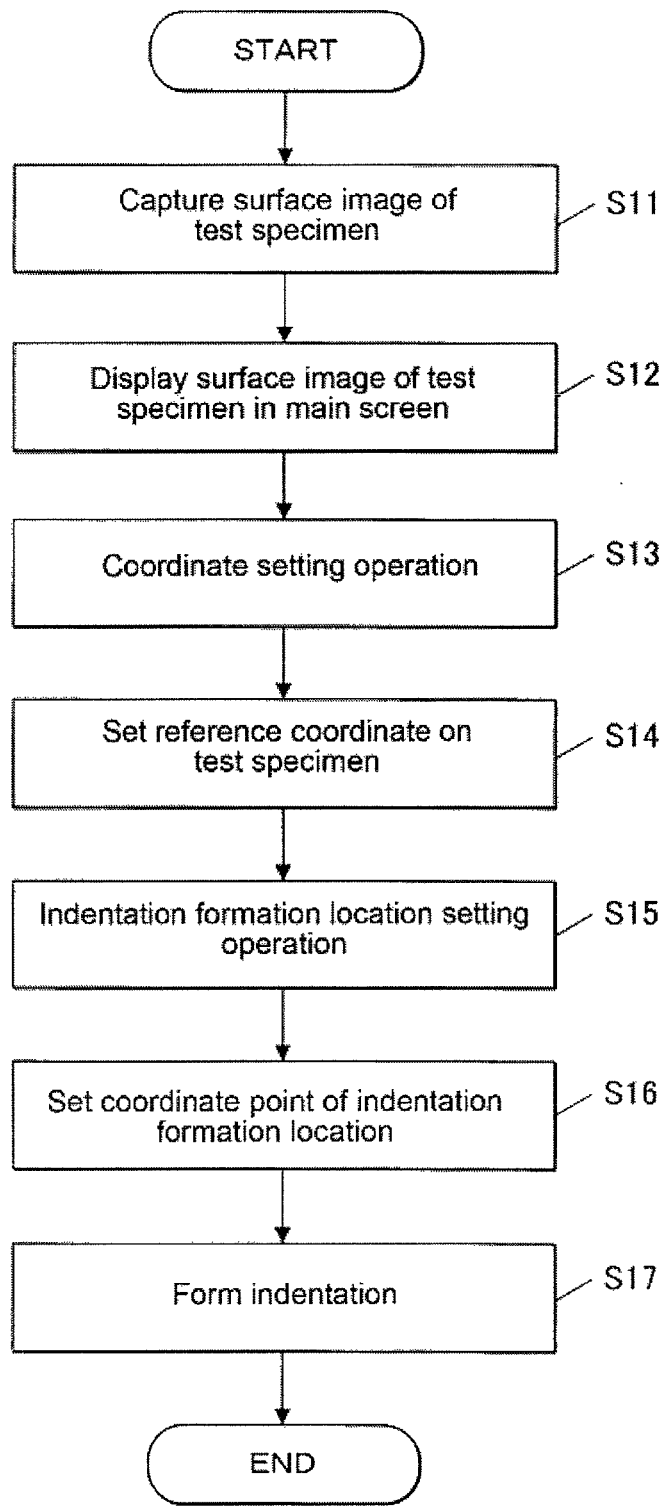
FIG. 11 is a flowchart illustrating a first test location setting process in FIG. 10.
Figure 12:
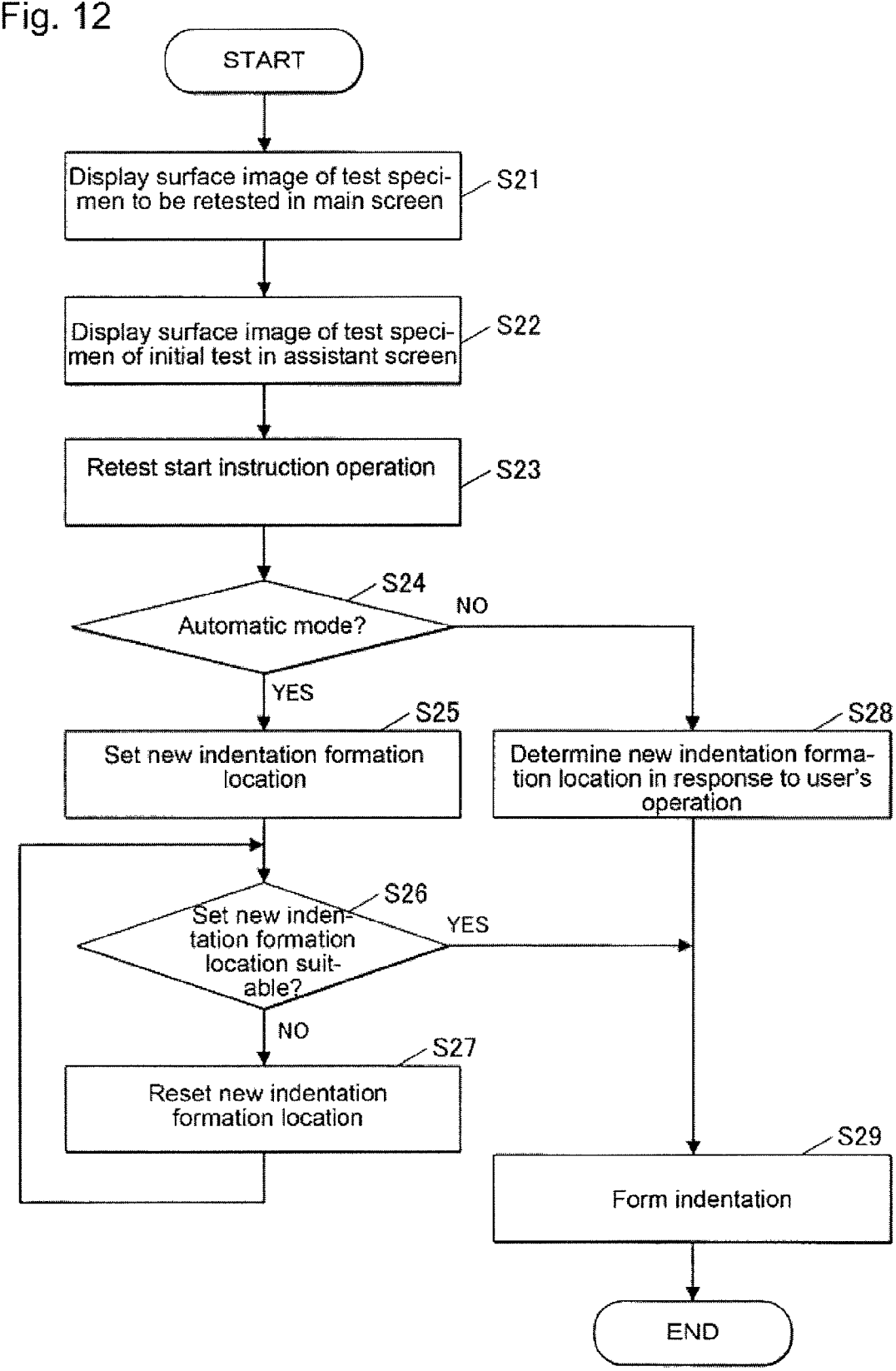
FIG. 12 is a flowchart illustrating a second test location setting process in FIG. 10.

Next, a measurement process of the hardness tester 100 is explained using flowcharts illustrated in FIGS. 10-12. As illustrated in FIG. 10, the measurement process of the hardness tester 100 includes a first test location setting process (step S10) setting an indentation formation location with respect to a test specimen S during an initial test, and a second test location setting process (step S20) setting a new indentation formation location with respect to the test specimen S during a retest.

FIG. 11 is a flowchart illustrating the first test location setting process. First, at a step S11, the CPU 61 captures a surface image of a test specimen S using the CCD camera 12. Next, at a step S12, the CPU 61 displays the surface image of the test specimen S in the main screen A1 on the monitor 8. The surface image (initial image) of the test specimen S is stored in the image storage 63*e*. Next, at a step S13, a user performs a coordinate setting operation with respect to the surface image of the test specimen S. A location specified by the coordinate setting operation is overlappingly displayed on the surface image of the test specimen S, and this image is stored in the image storage 63*e*. Next, at a step S14, the CPU 61 sets a reference coordinate on the surface image of the test specimen S. The set reference coordinate is overlappingly displayed on the surface image of the test specimen S, and this image is stored in the image storage 63*e*. Next, at a step S15, the user performs an indentation formation location setting operation with respect to the surface image of the test specimen S. Next, at a step S16, the CPU 61 sets a coordinate point of an indentation formation location using the set reference coordinate. Next, at a step S17, the CPU 61 forms an indentation at the set coordinate point. The surface image having the indentation formed on the surface is stored in the image storage 63*e*.

FIG. 12 is a flowchart illustrating the second test location setting process. First, at a step S21, the CPU 61 displays the surface image of the test specimen S to be retested in the main screen A1 on the monitor 8. Next, at a step S22, in response to an image read-out operation by the user, the CPU 61 displays the surface image of the test specimen S captured during the initial test in the assistant screen A2 on the monitor 8. Next, at a step 23, the user performs a retest start instruction operation. Next, at a step S24, the CPU 61 judges whether setting of a new indentation formation location is performed in the automatic mode. In a case where it is judged that it is performed in the automatic mode (step S24: YES), at a following step S25, the CPU 61 sets a new indentation formation location based on the setting condition stored in the setting condition storage 63*d*. Next, at a step S26, the CPU 61 judges whether the set new indentation formation location is suitable for a hardness test. In a case where it is judged that it is suitable (step S26: YES), the process proceeds to a step S29 described below. On the other hand, in a case where it is judged that the set new indentation formation location is unsuitable for a hardness test (step S26: NO), the CPU 61 performs a re-setting of the new indentation formation location at a following step S27, and returns the process to the step S26 and repeats the steps thereafter. At the step S24, in a case where it is judged that the setting of the new indentation formation location is not performed in the automatic mode (step S24: NO), at a subsequent step S28, the CPU 61 determines a new indentation formation location according to a retest location specifying operation by the user. Next, at the step S29, the CPU 61 forms an indentation. The surface image having the indentation formed on the surface is stored in the image storage 63*e*.

As described above, according to the hardness tester 100 of the present embodiment, in the case where a retest is performed, based on the setting condition stored in the setting condition storage 63*d*, the CPU 61 sets a coordinate point that is different from the coordinate point of the indentation formation location on the test specimen S as a new indentation formation location on the test specimen S; and, based on the brightness value of the surface image of the test specimen S stored in the image storage 63*e*, the CPU 61 judges whether the new indentation formation location is suitable for a test. In the case where the new indentation formation location is judged as unsuitable for a test, the CPU 61 again sets a coordinate point that is different from the coordinate point of the new indentation formation location as another new indentation formation location. Thus, a location that is suitable as a new indentation formation location is automatically set, and a retest is performed. Therefore, operability can be improved in the case where a retest is performed with respect to a test specimen S that has been tested once.

Further, according to the hardness tester 100 of the present embodiment, in the case where a retest start instruction operation is performed by a user, based on the setting condition stored in the setting condition storage 63*d*, the distance between the edge of the test specimen S and the coordinate point set as the indentation formation location during the initial test is calculated. A coordinate point that has a distance from the edge of the test specimen S equal to the calculated distance and is different from the coordinate point set during the initial test is selected as a new indentation formation location. Thus, a retest can be performed at a point different from that of the initial test, with the distance from the edge of the test specimen S unchanged. Therefore, even in the case where a retest is performed, evaluation of hardness distribution based on distance (depth) from the edge of the test specimen S can be favorably performed.

Further, according to the hardness tester 100 of the present embodiment, in the case where two coordinate points having equal distances from the edge of the test specimen S are set as indentation formation locations, on a line connecting the two points along the shape of the edge of the test specimen S, a coordinate point of a point at the middle of the two points is selected as a new indentation formation location. Therefore, a locations that is least affected by the initial test is selected as a new indentation formation location.

Further, according to the hardness tester 100 of the present embodiment, it is possible to switch between an automatic mode and a manual mode. In the case where a retest is performed in the manual mode with respect to the test specimen S, when a retest location specifying operation is performed by a user with respect to the surface image of the test specimen S displayed in the main screen A1, in response to this operation, a new indentation formation location is set. Therefore, it is possible to switch to an automatic mode or a manual mode depending on the test specimen S. In the manual mode, a user can visually specify any point as a new indentation formation location. Therefore, a favorable method can be selected according to the test specimen S, and a good operability can be achieved.

The present invention is not limited to the above embodiments, but can be modified as appropriate within the scope without departing from the spirit of the present invention. For example, during a retest, it is also possible to overlappingly display the imaginary lines K1-K3 calculated by executing the distance calculation program 63g on the surface image of the test specimen S displayed in the assistant screen A2. In this case, even better operability for a user can be achieved in the manual mode.

Further, in the above embodiment, a case is described as an example where a plurality of indentations are formed on a plurality of normal lines of equal pitch on an arc-shaped test specimen S, and an indentation is formed in a retest between neighboring normal lines. However, the shape of the test specimen S is not limited to this. Further, the indentation formation location and the number of indentations are also not limited to this. For example, the present invention is also applicable to a case where the shape of the edge of the test specimen is of a straight line. Further, in a case where the number of formed indentations is one, a new indentation formation location may be set a pre-set distance away. Further, a way to set the X axis and the Y axis is also not limited to the above embodiments.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester for forming an indentation on a surface of a test specimen mounted on a test specimen stage by pressing an indenter loaded with a predetermined load against the surface of the test specimen, comprising:
    a display configured to display a main screen and an assistant screen, the main screen configured to display a surface image of the test specimen, on which an indentation is formed by the indenter, and the assistant screen configured to display an assistant image to assist a user;
    a first test location setter configured to set a test location on the test specimen when an initial test is performed with respect to the test specimen; and
    a second test location setter configured to set a test location on the test specimen when a retest is performed with respect to the test specimen,
    the first test location setter comprising:
        a first coordinate setter configured to set a reference coordinate on the surface image of the test specimen when the surface image of the test specimen is displayed on the main screen;
        an indentation formation location setter configured to set a coordinate point of an indentation formation location after the reference coordinate is set by the first coordinate setter;
        a setting condition store configured to store a setting condition of the coordinate point set by the indentation formation location setter; and
        an image store configured to store the surface image of the test specimen displayed on the main screen,
    the second test location setter comprising:
        an assistant image display controller configured to display, on the assistant screen as an assistant image, the surface image of the test specimen stored in the image store;
        a new indentation formation location setter configured to set a coordinate point with respect to the assistant image as a new indentation formation location based on the setting condition stored in the setting condition store when a retest start instruction operation is performed by a user, the coordinate point being different from the coordinate point set by the indentation formation location setter; and
        a judger configured to judge whether the coordinate point of the new indentation formation location set by the new indentation formation location setter is suitable for a hardness test based on a brightness value of the surface image of the test specimen stored in the image store,
    wherein when the coordinate point of the set new indentation formation location is judged as unsuitable for a hardness test by the judger, the new indentation formation location setter again sets a coordinate point of a new indentation formation location.

2. The hardness tester according to claim 1, further comprising a selector configured to select an automatic mode, in which a new indentation formation location is set by the new indentation formation location setter, and a manual mode, in which a new indentation formation location is set by a user, wherein the second test location setter further comprises a new indentation formation location determiner configured to determine a new indentation formation location in response to a retest location specifying operation by a user with respect to the surface image of the test specimen displayed on the main screen when the manual mode is selected by the selector.

3. The hardness tester according to claim 1, wherein the new indentation formation location setter comprises:

a distance calculator configured to calculate a distance from an edge of the test specimen to the coordinate point set by the indentation formation location setter based on the setting condition stored in the setting condition store in the case where the retest start instruction operation is performed by the user; and a new indentation formation location selector configured to select as a new indentation formation location a coordinate point that has a distance from the edge of the test specimen equal to the distance calculated by the distance calculator and is different from the coordinate point set by the indentation formation location setter.

4. The hardness tester according to claim 3, further comprising a selector configured to select an automatic mode, in which a new indentation formation location is set by the new indentation formation location setter, and a manual mode, in which a new indentation formation location is set by a user, wherein the second test location setter further comprises a new indentation formation location determiner configured to determine a new indentation formation location in response to a retest location specifying operation by a user with respect to the surface image of the test specimen displayed on the main screen when the manual mode is selected by the selector.

5. The hardness tester according to claim 3, wherein when coordinate points of two points having equal distances from the edge of the test specimen S are set as indentation formation locations by the indentation formation location setter, the new indentation formation location selector selects as a new indentation formation location a coordinate point of a midpoint of the two points on a line connecting the two points along a shape of the edge of the test specimen.

6. The hardness tester according to claim 5, further comprising a selector configured to select an automatic mode, in which a new indentation formation location is set by the new indentation formation location setter, and a manual mode, in which a new indentation formation location is set by a user, wherein the second test location setter further comprises a new indentation formation location determiner configured to determine a new indentation formation location in response to a retest location specifying operation by a user with respect to the surface image of the test specimen displayed on the main screen when the manual mode is selected by the selector.

* * * * *